(12) United States Patent
Jorczak et al.

(10) Patent No.: US 7,552,731 B2
(45) Date of Patent: Jun. 30, 2009

(54) REMOTE CONTROL GAS REGULATION SYSTEM

(75) Inventors: Kevin D. Jorczak, Florence, MA (US);
Matthew T. Kling, Uxbridge, MA (US);
Daniel Nelson, Milford, MA (US);
David S. Green, Boston, MA (US);
Leonard Polizzotto, San Francisco, CA (US)

(73) Assignee: Remcore, Inc., Boston, MA (US)

( * ) Notice: Subject to any disclaimer, the term of this patent is extended or adjusted under 35 U.S.C. 154(b) by 404 days.

(21) Appl. No.: 10/714,467

(22) Filed: Nov. 14, 2003

(65) Prior Publication Data

US 2005/0103342 A1 May 19, 2005

(51) Int. Cl.
*A61M 15/00* (2006.01)
(52) U.S. Cl. .............................. 128/205.24; 128/204.21
(58) Field of Classification Search ............ 128/204.18, 128/204.21–204.24, 205.24
See application file for complete search history.

(56) References Cited

U.S. PATENT DOCUMENTS

| | | | |
|---|---|---|---|
| 5,103,814 A * | 4/1992 | Maher ................... | 128/204.18 |
| 5,137,046 A | 8/1992 | Sollman et al. | |
| 5,603,315 A | 2/1997 | Sasso, Jr. | |
| 5,755,224 A | 5/1998 | Good et al. | |
| 5,839,434 A | 11/1998 | Enterline | |
| 5,865,174 A | 2/1999 | Kloeppel | |
| 5,873,359 A * | 2/1999 | Zapol et al. ............ | 128/203.12 |
| 5,890,490 A | 4/1999 | Aylsworth et al. | |
| 5,928,189 A | 7/1999 | Phillips et al. | |
| 6,142,149 A | 11/2000 | Steen | |
| 6,192,883 B1 | 2/2001 | Miller, Jr. | |
| 6,371,114 B1 | 4/2002 | Schmidt et al. | |
| 6,467,505 B1 | 10/2002 | Thordarson et al. | |
| 6,470,885 B1 | 10/2002 | Blue et al. | |
| 6,616,606 B1 * | 9/2003 | Petersen et al. ............. | 600/300 |
| 6,763,832 B1 * | 7/2004 | Kirsch et al. ........... | 128/207.18 |
| 7,225,809 B1 * | 6/2007 | Bowen et al. .......... | 128/204.21 |

* cited by examiner

*Primary Examiner*—Steven O Douglas
(74) *Attorney, Agent, or Firm*—Mintz, Levin, Cohn, Ferris, Glovsky and Popeo, PC (57) ABSTRACT

A gas regulation system is provided comprising a source of a breathable gas, a tube in communication with the source for delivering the breathable gas from the source to an individual, and a valve for controlling the rate of gas flow from the source to the individual for inhalation. A remote control unit for controlling the valve is also provided to allow the individual to adjust the rate of gas flow from the source through the tube to the individual independently from any inhalation activity by the individual. Typically, the system excludes any means for automatically adjusting the rate of gas flow from the source through the tube to the individual according to the level of physical activity of the individual. The invention is particularly useful when the valve is out of the individual's reach. Also provided is a method for delivering of a breathable gas to an individual.

49 Claims, 4 Drawing Sheets

REMOTE CONTROL GAS REGULATION SYSTEM

TECHNICAL FIELD

The invention relates generally to a gas regulation system for regulating and delivering a breathable gas such from a source via a valve to an individual. In particular, the invention relates to such a system for delivering a breathable medical gas in which a remote control unit is provided for controlling the valve. The remote control unit allows the individual to adjust the rate of gas flow independently from any inhalation activity by the individual.

BACKGROUND

Currently in the United States, 14 million people suffer from lung disease and/or experience chronic difficulties in breathing. In some instances, such individuals may suffer from diminished oxygen uptake into the body. For example, the lungs of such individuals are not able to sufficiently receive oxygen and discharge carbon dioxide. Regardless of the cause of the pulmonary ailments, even a partial disability of the pulmonary system may require enrichment or supplementation of oxygen gas. The need for oxygen supplementation is particularly acute for persons suffering from Chronic Obstructive Pulmonary Disease (COPD) such as, emphysema and chronic bronchitis. In extreme instances, a severely compromised respiratory system may be incapable of supplying the necessary oxygen level for an individual at rest. As a result, supplemental oxygen must be delivered to such an individual to maintain the amount of oxygen at an acceptable level.

As a result, devices and systems for regulating the delivery of supplemental oxygen are known in the art. Typically, a stationary source of oxygen is provided having a tube attached thereto for supplying oxygen to the individual. For example, the source may be a tank reservoir containing pressurized medical quality oxygen. A flow regulator comprising one or more adjustable valves may be provided at the source to control the rate of oxygen flow from the tank through the tube to deliver oxygen to the patient by way of a nasal cannula, breathing mask, or transtracheal oxygen delivery system.

In general, there are two categories of such gas regulation systems, continuous flow and pulsed flow. As alluded to above, continuous flow devices and systems are generally set at a flow rate that provides the user with sufficient oxygen at all times, regardless of whether the user is inhaling or exhaling. Such continuous flow device and systems are generally described in U.S. Pat. No. 6,467,505 to Thordarson et al. A drawback associated such systems is that that the user only benefits from the supplemental oxygen during times in the respiratory cycle when the patient is inhaling in a manner which enables the supplemental oxygen to reach the lungs. At other times, the supplemental oxygen delivered is of no benefit, and is lost. Thus, when used with pressurized oxygen tanks of finite volume, such systems and devices require more frequent refilling and/or changing of the tanks.

In the alternative, pulsed flow systems may be employed to extend the time that a user may receive oxygen by providing oxygen to a user only when the user inhales. Such devices are described, for example, in U.S. Pat. No. 5,839,464 to Enterline. Typically, a burst of oxygen is delivered into a patient's nasal passages when a patient begins to inhale. This burst of oxygen is often uncomfortable for the patient. In addition, such high flow pulses generally cannot be tailored to the patient's physiological requirements or dynamically adjusted to meet the needs of the patient's changing activity level or breathing pattern. In addition, since the breathing pattern of users with compromised respiratory systems is often erratic, such pulse flow systems may exacerbate the user's breathing difficulties.

In healthy individuals, blood oxygen is regulated through the rate of respiration. With increasing activity level, an individual will breathe faster and/or more deeply to enhance oxygen delivery. Nevertheless, compromised pulmonary systems may be unable to supply the necessary oxygen levels required during increased activity. There is a need to deliver more oxygen to individuals with a compromised pulmonary system during periods of increased activity, i.e., walking to the bathroom, up steps, etc. When a stationary source of oxygen is provided, oxygen delivery rate may be altered by adjusting the oxygen flow at the source prior to undertaking the activity, and returning the oxygen flow rate to a lower level after the activity has been carried out. This is inconvenient when the regulator is out of reach. In addition, when the individual is away from the source, immediately changes the oxygen flow rate cannot be effected. Thus, individuals using this type of stationary gas delivery system often maintains the oxygen flow rate at a higher or lower level than necessary, i.e., during increased activity and at rest, which in turn, may creates a dependency upon the higher oxygen levels that is similar in effect to the use of a habit forming drug.

In some instances, known systems and devices automatically adjust the flow rate of oxygen to a person according to the person's activity level. For example, U.S. Pat. No. 5,928,189 to Phillips et al. describes an activity responsive therapeutic delivery system for delivering oxygen to a person in need of supplemental oxygen. The system is described as responsive to changes in the level of the person's activity. The system includes a source of oxygen, a means for delivering oxygen to a person, and a valve for delivery oxygen from the source to the person at two different flow rates. An activity sensor means is positioned to sense activity of the person, e.g., whether the person is standing or sitting, and to adjust the valve according to the sensed activity. In some instances, e.g., as described in U.S. Pat. No. 6,192,883 to Miller, Jr., the flow rate of oxygen may be adjusted using a manual override.

In addition, the flow of oxygen may be adjusted according to the breathing rate of an individual. For example, U.S. Pat. No. 5,865,174 to Kloeppel describes an apparatus and method that employs a pressure sensor to sense the pressure in the nasal passage of an individual receiving oxygen from a oxygen supply. A controller is provided in operative connection with the sensor. The controller controls a valve connected to the oxygen supply and automatically adjusts the flow rate of oxygen to be adjusted according to the pressure sensed by the sensor. Other examples of such oxygen flow rate regulation are described in U.S. Pat. No. 6,470,885 to Blue et al., U.S. Pat. No. 5,890,490 to Aylsworth et al., U.S. Pat. No. 5,755,224 to Good et al., and U.S. Pat. No. 5,603,315 to Sasso, Jr., Systems and devices that automatically adjust the flow rate of oxygen according to a patient's blood oxygen content are also known in the art. For example, U.S. Pat. No. 6,371,114 to Schmidt et al. describes systems for delivering respiratory oxygen to a patient. The system is comprised of a blood oxygen content level sensor (e.g., a pulse oximeter), a supplemental oxygen source, a valve in fluid communication with the supplemental oxygen source, and a controller capable of operating the valve. The controller restricts supplemental oxygen flow through the valve when the blood oxygen content level measured by the blood oxygen content level sensor is above a desired value. U.S. Pat. No. 6,147,149 to Steen provides another example of this type of oxygen flow rate regulator.

One unavoidable drawback of automatically adjustable devices and systems is that they require a sensor for operability. For example, when the sensor is used to monitor the user's respiration, the sensor may be placed in user's nose, elsewhere in the user's respiratory tract, or on the user's face for detecting the flow of oxygen. As another example, when the sensor is used to monitor the user's physical activity, motion sensor detectors often must be placed on or near regions of the user's body engaging in physical activity. As a further example, when the sensor is used to monitor the user's blood oxygen content, invasive techniques for obtaining blood or for positioning the sensor may be required. The sensors generally represent a source of discomfort or irritation for the user.

Another drawback for such devices and systems is that automatic adjustment mechanisms are often imperfect. Often, the response times associated with such mechanisms are inadequate and results in the delayed adjustment of oxygen delivery. For example, when an oximeter is used to measure blood oxygen saturation, a certain amount of time may be needed for blood to circulate to allow oxygen to reach the oximeter. As a result, the delivery of oxygen often fails to reflect the actual demand by user. Because automatic adjustment systems are often associated with pulsed oxygen delivery, such systems may mot be suitable for use by patients with impaired pulmonary system who cannot tolerate pulsed delivery of oxygen.

Thus, there is a need in the art to overcome the shortcomings associated with known gas regulation technology by providing a system for delivering a breathable medical gas that includes a remote control unit to allow a user to adjust the delivery rate of gas flow.

SUMMARY OF THE INVENTION

In a first embodiment, the invention relates to a gas regulation system comprising a source of a breathable gas, a tube in communication with the source for delivering the breathable gas from the source to an individual, and a valve for controlling the rate of gas flow from the source to the individual for inhalation. A remote control unit for controlling the valve is also provided to allow the individual to adjust the rate of gas flow from the source through the tube to the individual independently from any inhalation activity by the individual. Typically, the system excludes any means for automatically adjusting the rate of gas flow from the source through the tube to the individual according to the level of physical activity of the individual. The invention is particularly useful when the valve is out of the individual's reach.

Typically, the invention is used to deliver a medical gas comprising oxygen at a concentration greater than atmospheric oxygen concentration.

In another embodiment, the invention provides a method for delivering of a breathable gas to an individual. The method involves directing breathable gas from a source of the breathable gas through a valve and a tube to an individual for inhalation, wherein the valve is adapted for controlling gas flow from the source and is not automatically adjusted according to the level of physical activity of the individual. In addition, the individual is allowed to adjust the rate of gas flow from the source using a remote control unit for controlling the valve independently from any inhalation activity by the individual flow. The method typically involves adjusting the flow rate to correspond to a flow rate prescribed by a medical professional such as a physician. The prescribed flow rates may be associated with the individual's need for the breathable gas at rest, with moderate activity, or with strenuous activity.

In a further embodiment, the invention relates to a gas regulation system for delivering gas from a source containing a breathable gas to an individual. A valve is provided comprising an inlet adapted to receive gas from the source, an outlet adapted to deliver gas to the individual, a means for altering gas flow from the inlet to the outlet, and a receiver for receiving a signal for controlling the means for altering gas flow. Also provided is a remote control unit for transmitting the signal for controlling the means for altering gas flow. The remote control allows the individual to control the rate of gas flow to the individual independently from any inhalation activity by the individual. No means is provided for automatically adjusting the rate of gas flow from the source through the tube to the individual according to the level of physical activity of the individual.

DETAILED DESCRIPTION OF THE INVENTION

Before the invention is described in detail, it is to be understood that, unless otherwise indicated, this invention is not limited to particular materials, components or manufacturing processes, as such may vary. It is also to be understood that the terminology used herein is for purposes of describing particular embodiments only, and is not intended to be limiting.

As used in the specification and the appended claims, the singular forms "a," "an" and "the" include plural referents unless the context clearly dictates otherwise. Thus, for example, reference to "remote control unit" includes a single remote control unit as well as a plurality of remote control units, reference to "an inlet" includes a single inlet as well as multiple inlets, reference to "a valve" includes a single valve as well as an assembly of valves, and the like.

In this specification and in the claims that follow, reference will be made to a number of terms that shall be defined to have the following meanings, unless the context in which they are employed clearly indicates otherwise:

The term "activity" is used herein in its ordinary sense to refer to the state or energy associated with an individual's body movement. Thus, for example, the term "physical activity" typically refers to the state or energy associated with the movement of an individual's body, resting, walking, lifting, climbing, etc. as distinguished from activity of the mind. Similarly, the term "inhalation activity" refers to the state or energy associated with an individual's drawing in of a breathable gas through the act of respiration.

The terms "automatic" or "automatically" are used in their ordinary sense to refer to actions or operations that take place independently from an individual's control. For example, "automatic" adjustment the flow rate of gas to an individual according to the level of the physical activity of the individual occurs independently from conscious input by the individual.

The term "frequency hopping" is used herein to describe a technique typically associated with wireless signal transmission methods, wherein a signal is initially transmitted at a first frequency and later transmitted at a different frequency to provide a mechanism for low probability of intercept and resistance to jamming.

"Optional" or "optionally" as used herein means that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not. Mere reference to a feature, structure, event or circumstance as "optional," does not imply in any way whether the feature, structure, event or circumstance is be preferred.

The term "remote control unit" is used in its ordinary sense to refer to a unit capable of controlling a machine or apparatus from a distance. As used herein, the term typically refers to a unit for controlling a valve that controls flow of breathable gas flow from a source to an individual.

The term "substantially" as in "substantially constant flow rate" is used herein to refer to a flow rate that does not differ by more than approximately 15%. Preferably, the flow rates do not differ by more than 5% and optimally by not more than approximately 1%. Other uses of the term "substantially" have an analogous meaning.

In general, the invention fulfills the need for a gas regulation system that allows an individual to control, remotely or otherwise, the delivery of breathable gas, e.g., oxygen, to the individual on an as-needed and/or desired flow rate. In certain embodiments, a source of a breathable gas is provided having a tube in communication therewith for delivering the breathable gas from the source to an individual. A valve controls the rate of gas flow from the source to the individual, and a remote control unit controlling the valve to allow the individual to adjust the rate of gas flow from the source through the tube to the individual independently from any inhalation activity by the individual. The system provided overcomes the drawback associated with known devices by excluding any means for automatically adjusting the rate of gas flow from the source through the tube to the individual according to the level of physical activity of the individual.

Such systems are well suited for use in conjunction with "ramp-down" and "fail-safe" operation by individuals having a compromised respiratory system, particular during changes in activity level. For example, patients who suffer from COPD need externally delivered oxygen therapy at an appropriate rate in order to breathe correctly, both at home and in hospitals. For these patients, physicians often prescribe different oxygen flows for different activities, e.g., 2 liters per minute for a patient at rest and 5 liters per minute for a patient engaged in a more vigorous physical activity.

In order to provide such patients control over the rate of oxygen flow according to their activity level, the invention also provides a method for delivering of a breathable gas to an individual. The method involves directing breathable gas from a source of the breathable gas through a valve and a tube to an individual for inhalation. The valve is adapted for controlling gas flow from the source and allowing the individual to adjust the rate of gas flow from the source using a remote control unit for controlling the valve independently from any inhalation activity by the individual.

To avoid the disadvantages associated with known devices, the rate of gas flow and is not automatically adjusted by the system according to the level of physical activity of the individual. Instead, the invention allows the individual to adjusted the flow rate to a prescribed or desired flow rate, e.g., associated with the individual's need for the breathable gas at rest, with moderate activity, or with strenuous activity.

Figure 1A:
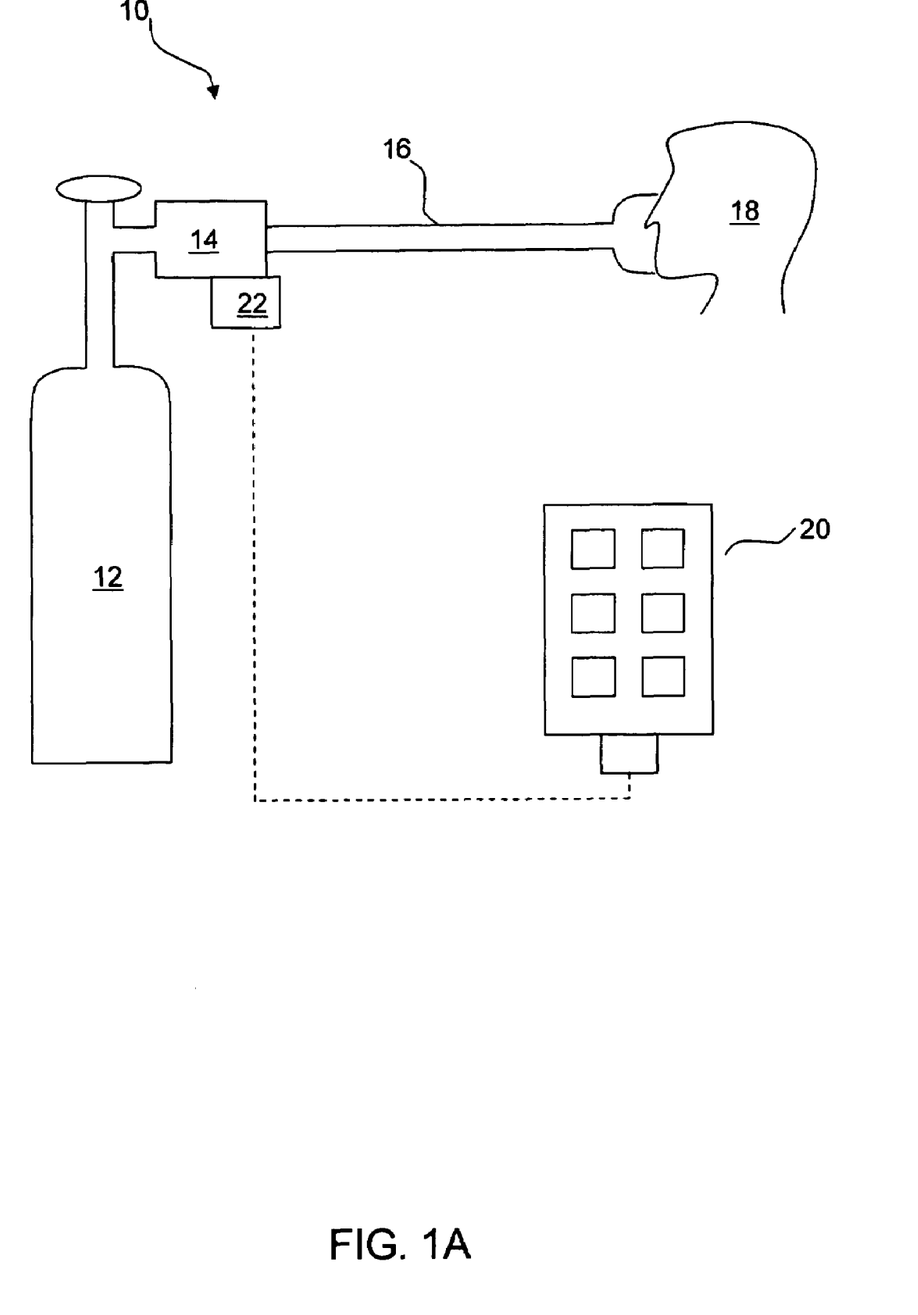
FIG. 1A is a schematic illustration of an exemplary gas regulation system of the present invention.
Figure 1B:
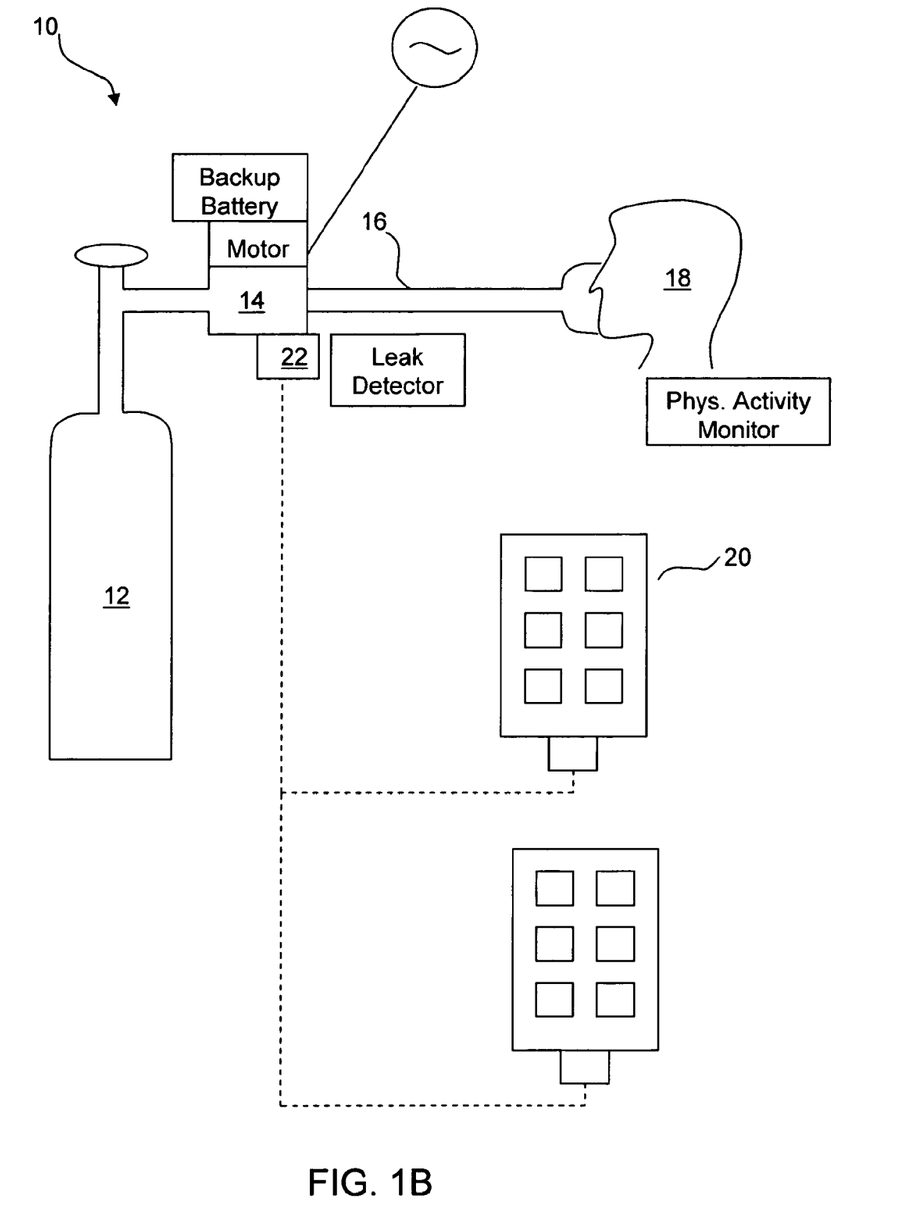
FIGS. 1B and 1C are schematic illustrations of exemplary gas regulation systems of the present invention showing additional features beyond those depicted in FIG.1A.
Figure 1C:
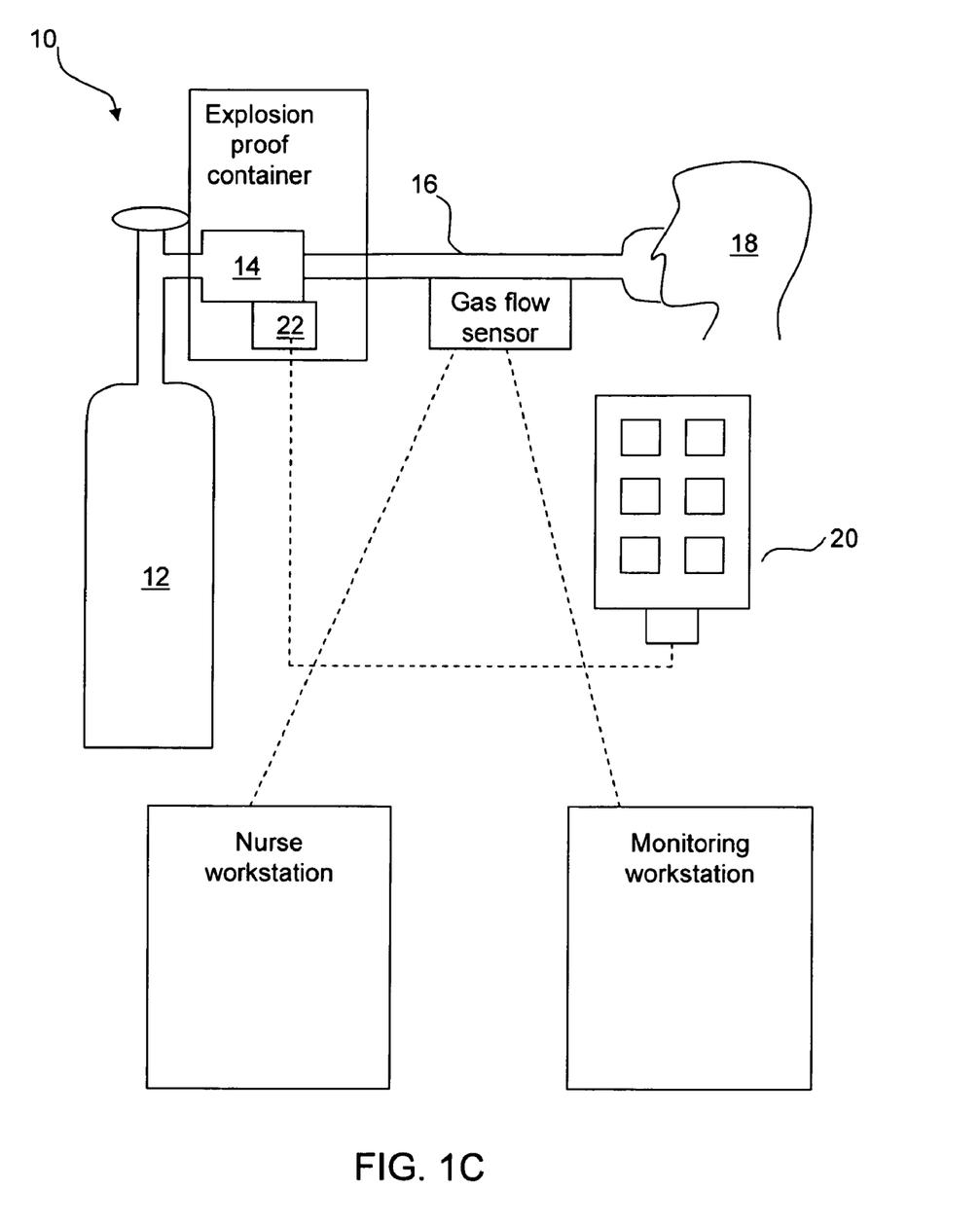

The inventive system contains components typically included in an ordinary oxygen regulation system but also includes a number of modifications. FIGS. 1A-1C depict exemplary embodiments of the inventive system. As with all figures referenced herein, in which like parts are referenced by like numerals, FIGS. 1A-1C are not necessarily to scale, and certain dimensions may be exaggerated for clarity of presentation. As depicted, the system 10 includes a source of oxygen in the form of an oxygen tank 12. An oxygen regulator comprising a solenoid valve 14 is operatively connected and located downstream from the tank 12. A tube 16 is also attached the valve 14 to transport to oxygen to a patient 18. The valve 14 is adapted to control the oxygen flow-rate based on a control signal received thereby.

Also provided is a remote control unit 20 for controlling the valve. Typically constructed as a hand held unit, the control unit 20 is adapted to generate a control signal to allow the patient to select an appropriate oxygen flow rate from the oxygen tank 12. As depicted, the signal is transmitted through a wireless link to a receiver 22 for receiving the control signal. The receiver 22 is depicted in operative communication with the solenoid valve 14. Optionally, a translator is provided to translate the control signal to maintain or alter the flow of oxygen that is delivered through the valve 14 to the patient 18.

The invention is particularly suited for use with a medical gas such as oxygen, nitrous oxide, medical air, nitrogen, etc. For oxygen therapy, oxygen is generally provided at a concentration greater than atmospheric oxygen concentration. Thus, for example, the source may include a tank containing medical gas comprised of oxygen. Typically, such tanks are contaminant-free and capable of containing pressured and/or liquefied gas. Often such tanks are made from steel or aluminum. Steel tanks are typically tested every 10 years for structural damage, whereas aluminum tanks are tested every 5 years for cracks, dents, burns, dings, oil, grease, corrosion, and other type of damage.

Typically, oxygen cylinders provide about 2 L/min to 15 L/min of oxygen. While more expensive, the liquid oxygen tanks can deliver oxygen for four times longer than the normal tanks. In addition or in the alternative, the source may comprise an oxygen concentrator. Concentrators extract oxygen from air for delivery in a concentrated form.

Oxygen regulators may be used to control and reduce the pressure of the oxygen from a tank containing compressed or liquid oxygen for safe and steady gas delivery to a patient. The regulator typically contains or is used in conjunction with a valve. Such a valves are typically comprised an inlet adapted to receive gas from the source, an outlet adapted to deliver gas to the individual, and a means for altering gas flow from the inlet to the outlet. Although gas flow through the valve may be altered, the valve is typically constructed so that it is capable of providing a substantially constant flow rate of the gas flow to the individual.

Any number of known means for altering gas flow may be employed. Exemplary means for altering gas flow include, but are not limited to, linearly or rotationally actuated switching mechanisms such as those associated with gate and ball valves, respectively. Typically, the valve is electrically powered and/or actuated. Thus, for example, the valve may be provided comprising a motor in electrical connection with a source of alternating electrical current. In addition or in the alternative, a direct current backup battery may be provided for powering the valve. Additional or alternative means such as hydraulic may be used to power and/or actuate the switching mechanism as well. Regardless of the means employed to power and/or actuate the switching mechanism, it is preferred that the valve be manually operative when the power source is inoperative. For example, in case of an AC power failure, the system should have a battery backup power source, which would allow the system to run for a short period of time while the patient switches the electronic system to be bypassed, so that the manual controlled oxygen regulator can be used.

As alluded to above, solenoid valves are particularly useful in the invention. Such valve typically employ a coil and a core that slides along under the influence of the magnetic field generated as a result of electrical current passed through the coil. The core serves as plunger to open or close a valve. Simple solenoid valves provide no control over the degree to which the valve is open or closed. Proportional solenoid valves, on the other hand, uses a variable input voltage and/or current o control the degree to which the valve is open or closed. The applied voltage and/or current are generally proportional to the amount of flow that the valve will provide. Proportional solenoid valves can provide precise regulation of flow, can typically operate anywhere from 0 to about 500 pounds per square inch, are very small and compact, and can operate under fairly rugged conditions.

In general, any remote control unit may be used that is suitable for controlling the valve so as to allow the individual to adjust the rate of gas flow from the source through the tube to the individual independently from any inhalation activity by the individual. In some instances, the remote control unit may be attached to the valve, e.g., via a hardwired connection. Alternatively, the remote control unit may be detached from the valve, e.g., wireless. Typically, though, a receiver is provided for receiving a signal from the remote control unit for controlling the valve or for controlling the means for altering gas flow. Preferably, the signal is electromagnetic in nature, and may include waves of radio frequency, microwave, infrared, and/or visible signal. The signal may be digital or analog. In any case, the system may be equipped for operation using a plurality of control signal frequencies, optionally with frequency hopping capability.

For example, the remote control system may employ a microprocessor-based design to implement a radio frequency (RF) communication set up to provide a wireless data transfer. Along with the remote control, an electromechanical element, e.g., a solenoid valve, serves to regulate the flow from the oxygen tank. RF systems can be implemented by using only a small number of electronic devices. These devices may include an antenna, a transmitter module and a receiver module, which are responsible for transmitting a signal. Optionally, the transmitter module modulates and/or amplifies the signal before transmission and the receiver module down-converts and/or demodulates the transmitted signal. Those of ordinary skill in the art will recognize that the selection of an appropriate microprocessor depends the capabilities of its central processing unit, memory, timer(s), port(s), software and other components. Printed circuit board technology may be employed with the microprocessor-based design described above. In some instances, the remote control system may be adapted to interface with a computer.

To provide an indication of gas flow rate, the system may further include a gas flow sensor positioned to detect and/or monitor the rate of gas flow to the individual. When such a sensor is employed, an indicator for indicating the rate of gas flow detected and/or monitored by the gas flow sensor is typically provided as well. Typically, the remote control unit houses such an indicator. In addition or in the alternative, one or more indicators may be located in a monitoring station, e.g., a nurses' station, as discussed below. In any case, the invention generally allows users to adjust their oxygen flow rates from zero to about 15 liters per minute.

Figure 2:
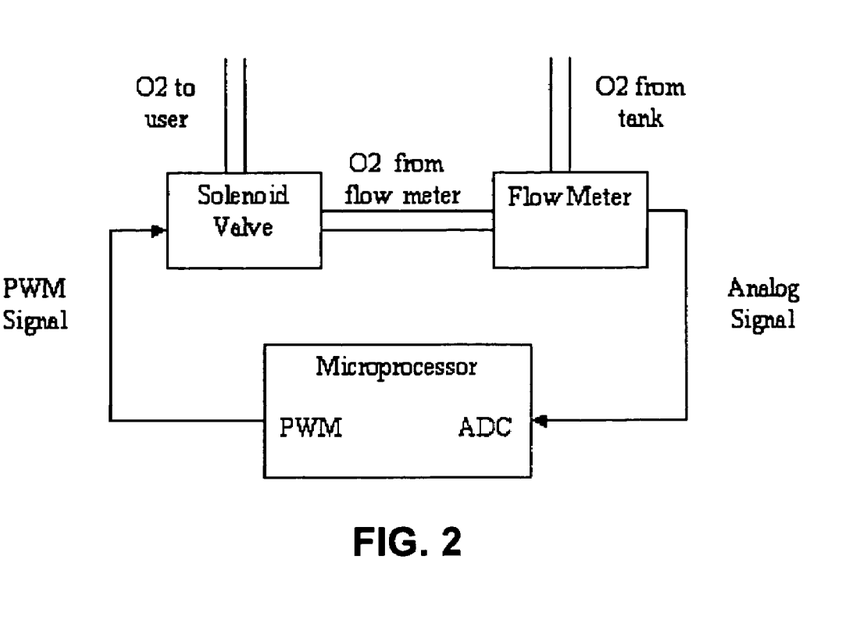
FIG. 2 is a schematic diagram that depicts an exemplary hardware and software feedback loop that may be used to provide an accurate and constant flow of gas to a patient.

FIG. 2 schematically depicts an exemplary hardware and software feedback loop that may be used to provide an accurate and constant flow of gas to a patient. A RF signal may be first signal from a remote control, e.g., to enter a desired flow rate, to increase the flow rate, or to decrease the flow rate. Typically, the signal is provided at a frequency in an unregulated industrial, scientific and medical (ISM) band. In addition, digital bit stream encoding such as frequency shift keying may be used to transmit the signal. In any case, the remote control signal should not interfere with other nearby wireless signals.

Meanwhile, the gas flow sensor is positioned to detect and/or monitor gas flowing therethrough. The flow sensor outputs an analog voltage that is directly proportional to the amount of flow through the device. The analog signal is then sent to an analog to digital converter (ADC) so that it can be processed by the microprocessor. The signal from the ADC is then used to determine whether the existing flow rate matches the desired flow-rate. If the software running on the microprocessor detects a difference between the existing and the desired flow rates, a signal is sent to the solenoid valve to adjust the flow rate accordingly. For example, a pulse width modulated (PWM) signal is a signal with a varying duty cycle, where the duty cycle is the amount of time that the signal is high versus the amount of time the signal is low. A PWM may be used to adjust the solenoid valve. The higher the duty cycle the more the valve will open and allow more oxygen to flow through the system.

For portability, the remote control unit is preferably a hand-held unit. In some instances, the remote control unit may be equipped to provide for fingertip adjustment of the rate of gas flow. Fingertip control may be In addition or in the alternative, the remote control unit may be sound activated unit that is optionally equipped to provide for voice recognition adjustment of the rate of gas flow. An analog and/or digital display may be included as well for indicating the rate of gas flow.

As discussed above, the remote control unit should be effective to control the valve from a remote location. In general, the range should be equal to or greater than the length of the tube for gas delivery. Regardless of the length of the tube, the remote control unit is typically effective for controlling the valve to a range of about 10 feet. Preferably, the remote control unit is effective for controlling the valve to a range of about 120 feet. Optimally the remote control unit is effective for controlling the valve to a range of about 300 feet. The actual range may depend on the location of use. For example, a typical American house is about 2,000 square feet in size. Thus, when the system is used in a typical American house, the remote control should be able to transmit at least 50 feet so as to remain functional throughout the house. In some instances, home use may require the remote control unit to have a transmission range up to 500 feet.

The remote control unit allows the user to change their oxygen flow in order to receive the correct amount of oxygen for their current activity. Preferably, the remote control unit is ergonomically designed so that it is easy to hold and use. For example, the remote control unit may be constructed to be worn like a wristwatch. In addition, lettering and display on the remote control should be fairly large and easily visible so that people with impaired vision are able to read it at all times.

Figure 3A:
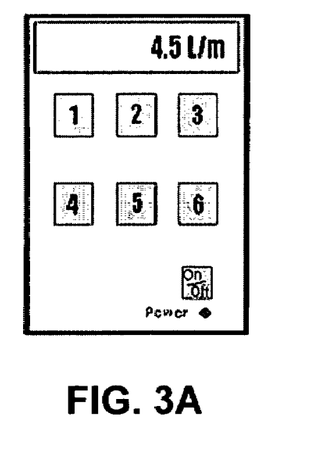
FIGS. 3A-3C, collectively referred to as FIG. 3, depict exemplary remote control user interfaces.
Figure 3B:
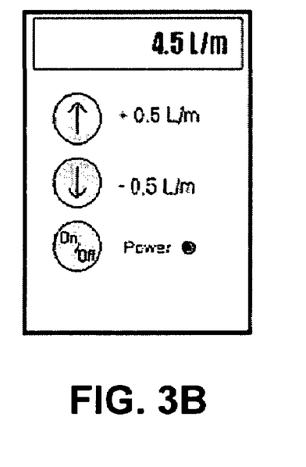
Figure 3C:
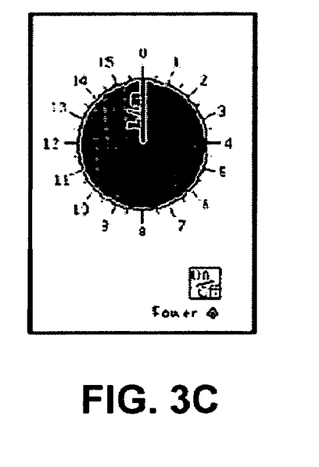

Exemplary user interfaces, e.g., provided by the remote control, are depicted in FIG. 3. For example, FIG. 3A depicts an interface that employs a button selection remote control. This interface utilizes a digital display to show the user the current oxygen flow. The buttons below the display are used to input the desired flow. In addition, FIG. 3B depicts an interface that also uses a digital display to show the user the current oxygen flow rate. Two buttons are provided on the remote to allow the user to change gas flow rate. One of the buttons allows for the flow rate of gas to be increased by preset increments while the other button is used to decrease the flow rate by the same preset value. Furthermore, FIG. 3C depicts a dial interface. When using this remote the user would use the dial to point to the desired oxygen flow rate. This interface does not require a digital display because the flow-rates are displayed directly next to the dial.

Although the inventive system does not automatically adjust rate of gas flow, a means for monitoring the level of blood oxygen or physical activity of the individual may be provided. In such instances, the system may also include an indicator for indicating the level of blood oxygen or physical activity monitored by the monitoring means. In general, a patient's oxygen saturation level should be at least 90%. Depending on the health and the activity level of an individual, the individual typically requires a flow rate between 0 and 15 liters per minute to keep his or her blood oxygen saturation level at 90% or higher.

A means for monitoring an individual's oxygen level is particularly advantageous for patients who suffer from COPD such as emphysema. For example, oxygen treatment is typically given to patients whose lung oxygen level is below 55 mm/Hg when resting, or if the patient has an oxygen level below 60 mm/Hg and also has other heart problems. Enough oxygen should be given to the patient to keep the level between 60 and 65 mm/Hg. Another consideration is that the oxygen during a plane ride in a depressurized cabin should be increased by 1-2 liters per minute. Such monitoring means may help in determining whether oxygen flow rate should be altered.

To monitor the oxygen saturation level in blood, pulse oximetry techniques may be employed. Pulse oximetry involves a measure of oxygen saturation in a patient's hemoglobin, and is a particularly useful diagnostics tool for monitoring patients who have problems absorbing oxygen into their blood from their lungs. Typically, oxygen saturation is measured via spectrophotometry. While oximetry may be carried out in either transmissive or reflective mode, both modes require a light source and a sensor, which are generally placed on an extremity, usually the finger, ear lobe, or the bridge of the nose, to sense the oxygen level in the blood. For example, a finger pulse oximeter may include two light emitting diodes (LEDs) at different wavelengths, 660 nanometers and 940 nanometers, and the sensor is a semiconductor detector, or a photodetector. These two wavelengths are associated with the absorbance wavelengths associated with deoxygenated and oxygenated hemoglobin, respectively.

As alluded to above, automatic adjustment mechanisms associated with oxygen delivery systems are often imperfect. Often, the response times associated with such mechanisms are inadequate and results in the delayed adjustment of oxygen delivery. For example, when oxygen first enters the body, it takes an additional 15-30 seconds for it to reach the extremities of the body. Thus, when an oximeter is used at the extremities for automatic adjustment of oxygen flow rate, the lag time for adjustment will be about 15-30 seconds. Accordingly, the invention provides a faster response time than an automatic adjusting system using oximetry. Nevertheless, pulse oximetry may provides the user with a quantitative measure of oxygen delivery.

When used in conjunction with oxygen and other flammable medical gases, valves and other components of the invention must be constructed with safety precautions in mind. For instance, explosion-proof and/or watertight solenoid valves are commercially available. When one or more motors are used actuate a valve, any motors used should be non-sparking. That is, the motor must have no normally arcing parts or thermal effects capable of ignition. Examples of normally arcing parts include, but are not limited to, relays, circuit breakers, servo-potentiometers adjustable resistors, switches, non-latching type connectors and motor brushes. Preferably, the motors are also explosion proof. That is, the motor may be enclosed in a case that is capable of withstanding an explosion of a specified gas or vapor that may occur therein. Optimally, the motor is constructed to operate at sufficiently low an external temperature that a surrounding flammable atmosphere will not be ignited thereby. Explosion proof motors are available from manufacturers such as Teco-Westinghouse Motor Company (Round Rock, Tex.) and Rockwell Automation, Inc (Milwaukee, Wis.). Similarly, explosion-proof containers may be employed for containing the valve or any other component that may ignite a flammable medical gas.

To promote safety and to maintain the proper functioning of the valve, the system may include a leak detector for detecting for a leak associated with the valve. Such a leak detector may represent a component of an error detection system. For example, the leak detector may be constructed to warn the user whenever a leak is detected; the user would then be warned to place the system into manual mode. Alternatively, the system could place itself into manual mode.

In addition, the error detection system may include fail-safe modes of operation. For example, in case of system failure, the system may provide a warning signal and deliver oxygen at a pre-specified flow rate, e.g., determined by the patient's doctor. In addition, a means for emergency shutoff of the gas flow may be provided as well.

In some instances, a monitoring station may be provided in addition to the remote control unit. Such a monitoring station may be stationary or mobile. For example, a monitoring system may be constructed as a nurse workstation for controlling a plurality of valves and is equipped with an indicator for each valve controlled thereby. Such a nurse station may be provided as standard hospital equipment to allow a single attendant to monitor and adjust the oxygen flow rates to a plurality of patients undergoing oxygen therapy. In addition, such a station may be interfaced to a computer. One of ordinary skill in the art will recognize that software may be developed for organizing, displaying, and or printing information about regarding oxygen usage.

Variations of the invention, not explicitly disclosed herein, will be apparent to those of ordinary skill in the art. For example, additional remote control units for controlling the valve may be provided. In such a case, a single control unit may override any signal from another control unit for controlling the valve. Furthermore, the invention may be adapted to nonmedical applications, e.g., environmental controls.

It is to be understood that while the invention has been described in conjunction with the preferred specific embodiments thereof, that the foregoing description illustrates but does not limit the scope of the invention. Other aspects, advantages and modifications within the scope of the invention will be apparent to those skilled in the art to which the invention pertains.

All patents, patent applications, patent publications and non-patent literature references mentioned herein are incorporated by reference in their entireties.

We claim:

1. A gas regulation system comprising:
   a source of a breathable gas;
   a tube in communication with the source for delivering the breathable gas from the source to an individual;
   a valve for controlling the rate of gas flow from the source to the individual for inhalation; and
   a remote control unit for controlling the valve so as to allow the individual to adjust the rate of gas flow from the source through the tube to the individual independently from any inhalation activity by the individual,
   wherein the system excludes any means for automatically adjusting the rate of gas flow from the source through the tube to the individual according to the level of physical activity of the individual.

2. The system of claim 1, wherein the breathable gas is a medical gas.

3. The system of claim 2, wherein the source is a tank containing the breathable medical gas.

4. The system of claim 2, wherein the breathable medical gas is comprised of oxygen.

5. The system of claim 4, wherein breathable medical gas contains oxygen at a concentration greater than atmospheric oxygen concentration.

6. The system of claim 1, wherein the source is an oxygen concentrator.

7. The system of claim 1, wherein the remote control unit is attached to the valve.

8. The system of claim 1, wherein the remote control unit is detached from the valve.

9. The system of claim 1, further comprising a control signal receiver for receiving an electromagnetic control signal for controlling the valve, wherein the remote control unit is adapted to transmit the electromagnetic control signal.

10. The system of claim 9, wherein the receiver is comprised of a translator for translating the control signal for controlling the valve.

11. The system of claim 9, wherein the electromagnetic control signal is a radio frequency, microwave, infrared, or visible signal.

12. The system of claim 9, wherein the control signal is digital.

13. The system of claim 9, wherein the signal is analog.

14. The system of claim 9, equipped for operation using a plurality of control signal frequencies.

15. The system of claim 14, equipped with frequency hopping capability.

16. The system of claim 1, wherein the remote control unit is a handheld unit.

17. The system of claim 16, wherein the remote control unit is equipped to provide for fingertip adjustment of the rate of gas flow.

18. The system of claim 1, wherein the remote control unit is a sound activated unit.

19. The system of claim 18, wherein the remote control unit is equipped to provide for voice recognition adjustment of the rate of gas flow.

20. The system of claim 1, wherein the remote control unit includes a display for indicating gas flow rate.

21. The system of claim 20, wherein the display is a digital display.

22. The system of claim 20, wherein the display is an analog display.

23. The system of claim 1, wherein the remote control unit is effective for controlling the valve to a range of about 10 feet.

24. The system of claim 23, wherein the remote control unit is effective for controlling the valve to a range of about 120 feet.

25. The system of claim 24, wherein the remote control unit is effective for controlling the valve to a range of about 300 feet.

26. The system of claim 1, wherein the remote control unit is effective for controlling the valve to a range equal to or greater than the length of the tube.

27. The system of claim 1, wherein the valve comprises a motor.

28. The system of claim 1, wherein the valve provides a substantially constant flow rate of the breathable gas to the individual.

29. The system of claim 1, further comprising an explosion-proof container containing the valve.

30. The system of claim 1, in electrical connection with a source of alternating electrical current for powering the valve.

31. The system of claim 30, further comprising a backup battery for powering the valve when the source of alternating electrical current is inoperative.

32. The system of claim 30, wherein the valve is manually operative when the source of alternating electrical current is inoperative.

33. The system of claim 1, further comprising a leak detector for detecting for a leak associated with the valve.

34. The system of claim 1, further comprising an additional remote control unit for controlling the valve.

35. The system of claim 34, wherein a single control unit overrides any signal from another control unit for controlling the valve.

36. The system of claim 1, further comprising a gas flow sensor positioned to detect and/or monitor the rate of gas flow to the individual.

37. The system of claim 36, wherein the gas flow sensor represents a component of an error detection system.

38. The system of claim 36, further comprising an indicator for indicating the rate of gas flow detected and/or monitored by the gas flow sensor.

39. The system of claim 38, wherein the indicator is located in the remote control unit.

40. The system of claim 38, wherein the indicator is located in a monitoring station.

41. The system of claim 40, wherein the monitoring station is a nurse workstation for controlling a plurality of valves and is equipped with an indicator for each valve controlled thereby.

42. The system of claim 1, further comprising a means for monitoring the level of physical activity of the individual.

43. The system of claim 42, further comprising an indicator for indicating the level of physical activity monitored by the monitoring means.

44. A method for delivering of a breathable gas to an individual, the method comprising:
   (a) directing breathable gas from a source of the breathable gas through a valve and a tube to an individual for inhalation, wherein the valve is adapted for controlling gas flow from the source and is not automatically adjusted according to the level of physical activity of the individual; and (b) allowing the individual to adjust the rate of gas flow from the source using a remote control unit for controlling the valve independently from any inhalation activity by the individual flow.

45. The method of claim 44, wherein the rate of gas flow is adjusted by the individual to a prescribed flow rate.

46. The method of claim 45, wherein the prescribed flow rate is associated with the individual's need for the breathable gas at rest.

47. The method of claim 45, wherein the prescribed flow rate is associated with the individual's need for the breathable gas with moderate activity.

48. The method of claim 45, wherein the prescribed flow rate is associated with the individual's need for the breathable gas with strenuous activity.

49. A gas regulation system for delivering gas from a source containing a breathable gas to an individual, comprising:
  a valve comprised of
    an inlet adapted to receive gas from the source,
    an outlet adapted to deliver gas to the individual,
    a means for altering gas flow from the inlet to the outlet, and
    a receiver for receiving a signal for controlling the means for altering gas flow; and
  a remote control unit for transmitting the signal for controlling the means for altering gas flow,
wherein the remote control allows the individual to control the rate of gas flow to the individual independently from any inhalation activity by the individual, and the system excludes any means for automatically adjusting the rate of gas flow from the source through the tube to the individual according to the level of physical activity of the individual.

* * * * *